(12) United States Patent
Riedel et al.

(10) Patent No.: US 11,110,228 B2
(45) Date of Patent: Sep. 7, 2021

(54) COMPONENT FOR AN INJECTION DEVICE, SYSTEM, AND METHOD

(71) Applicant: SANOFI-AVENTIS DEUTSCHLAND GMBH, Frankfurt am Main (DE)

(72) Inventors: Stephan Riedel, Frankfurt am Main (DE); Peter Scharf, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 684 days.

(21) Appl. No.: 15/775,506

(22) PCT Filed: Nov. 21, 2016

(86) PCT No.: PCT/EP2016/078248
§ 371 (c)(1),
(2) Date: May 11, 2018

(87) PCT Pub. No.: WO2017/089260
PCT Pub. Date: Jun. 1, 2017

(65) Prior Publication Data
US 2018/0361077 A1 Dec. 20, 2018

(30) Foreign Application Priority Data
Nov. 27, 2015 (EP) .................................... 15196676

(51) Int. Cl.
*A61M 5/32* (2006.01)
*A61M 5/31* (2006.01)

(52) U.S. Cl.
CPC ........ *A61M 5/3204* (2013.01); *A61M 5/3202* (2013.01); *A61M 2005/312* (2013.01); *A61M 2205/0216* (2013.01); *A61M 2207/00* (2013.01)

(58) Field of Classification Search
CPC .............. A61M 5/2033; A61M 5/3202; A61M 5/3204; A61M 5/20; A61M 5/24;
(Continued)

(56) References Cited

U.S. PATENT DOCUMENTS 2,625,157 A * 1/1953 Lockhart ............... A61M 5/282
604/192
5,114,409 A * 5/1992 Kole .................... A61M 5/3213
428/134
(Continued)

FOREIGN PATENT DOCUMENTS

DE 102005054075 5/2007
FR 2913202 9/2008
(Continued)

OTHER PUBLICATIONS

International Preliminary Report on Patentability in International Application No. PCT/EP2016/078248, dated May 29, 2018, 9 pages.
(Continued)

*Primary Examiner* — Manuel A Mendez
(74) *Attorney, Agent, or Firm* — Fish & Richardson P.C.

(57) ABSTRACT

A component for an injection device is a combined needle shield and cap component that comprises a unitary compressible body moulded from rubber. The unitary compressible body has formed therein a cavity for shielding a needle, the cavity having an opening at a first end of the component and extending axially within the component. It also has formed thereon a grip arrangement comprising one or more shape features that permit gripping by a user of the component so as to facilitate the application of force by the user along the longitudinal axis of the component. The combined needle shield and cap component has a proximal end configured to be partly insertable into a body of an injection device. The outer surface of the compressible body has a
(Continued)

step profile at a location between the proximal end of the compressible body, which is configured to be inserted into the injection device, and an adjacent part of the compressible body, which is configured to remain outside of injection device, wherein the proximal end of the compressible body has a smaller diameter than the adjacent part of the compressible body.

20 Claims, 7 Drawing Sheets

(58) Field of Classification Search
CPC .. A61M 5/326; A61M 5/3213; A61M 5/2448; A61M 5/3245; A61M 5/3257
See application file for complete search history.

(56) References Cited

U.S. PATENT DOCUMENTS

| | | | |
|---|---|---|---|
| 6,719,732 B2 * | 4/2004 | Courteix | A61M 5/3202 604/192 |
| 2005/0171484 A1 * | 8/2005 | Jangula | A61M 5/3213 604/198 |
| 2008/0215013 A1 | 9/2008 | Felix-Faure | |
| 2009/0105661 A1 | 4/2009 | Chevallier et al. | |
| 2012/0215179 A1 | 8/2012 | Halili et al. | |
| 2013/0338603 A1 | 12/2013 | Roedle et al. | |

FOREIGN PATENT DOCUMENTS

| | | |
|---|---|---|
| JP | 2008-229328 | 10/2008 |
| JP | 2009-514634 | 4/2009 |
| JP | 2013-519415 | 5/2013 |
| JP | 2013-524916 | 6/2013 |
| JP | 2014-176767 | 9/2014 |
| WO | WO 2007/054333 | 5/2007 |
| WO | WO 2008/139330 | 11/2008 |
| WO | WO 2011/098831 | 8/2011 |
| WO | WO 2011/131996 | 10/2011 |
| WO | WO 2012/003221 | 1/2012 |

OTHER PUBLICATIONS

International Search Report and Written Opinion in International Application No. PCT/EP2016/078248, dated Feb. 21, 2017, 12 pages.

* cited by examiner

COMPONENT FOR AN INJECTION DEVICE, SYSTEM, AND METHOD

CROSS REFERENCE TO RELATED APPLICATIONS

The present application is the U.S. national stage entry under 35 USC § 371 of International Patent Application No. PCT/EP2016/078248, filed on Nov. 21, 2016, which claims priority to European Patent Application No. 15196676.9, filed on Nov. 27, 2015, the entire contents of each of which are incorporated herein by reference.

TECHNICAL FIELD

The present disclosure relates to a component for an injection device, to a system, and to a method.

BACKGROUND

Injection devices, such as auto-injectors, are known in the art for dispensing a medicament to an injection site of a user. Such injection devices typically comprise a body and a cap. A needle syringe is located in the body. The cap is removably attached to the body to shield the needle of the needle syringe. To dispense the medicament, the cap is first removed from the body to expose the needle syringe.

The needle syringe is typically supplied with a needle shield in place, that is, a rubber sleeve which is fitted tightly over the needle to seal and protect the needle. The rubber needle shield must also be removed from the needle syringe to expose the needle for injection. The needle can then inserted into the body of the user at the injection site to dispense the medicament.

The cap of the injection device is typically large and easily removed. However, the rubber needle shield may be difficult to hold and therefore difficult to remove from the needle syringe. The proximity of the rubber needle shield to the needle makes some users uncomfortable about removing the needle shield.

SUMMARY

In one embodiment, a component for an injection device is provided. The component is a combined needle shield and cap component comprising a unitary compressible body moulded from rubber. The unitary compressible body has formed therein a cavity for shielding a needle, the cavity having an opening at a first end of the component and extending axially within the component. It also has formed thereon a grip arrangement comprising one or more shape features that permit gripping by a user of the component so as to facilitate the application of force by the user along the longitudinal axis of the component.

This combined needle shield and cap component can simplify the use of an injection device by a user because it provides the functionality of both a needle shield and a cap whilst allowing a user to remove it with a single action. Moreover, the compressible rubber material and the grip arrangement permit a construction where the needle shield and cap component is retained sufficiently strongly within the injection device so that accidental removal of the cap is substantially prevented whilst also allowing the user to remove the cap from the injection device relatively easily.

The proximal end of the unitary compressible body may be configured to be partly insertable into a body of an injection device. This can help to facilitate the retention of the needle shield and cap component in the injection device prior to use whilst allowing the user to remove the cap and expose the needle for injection using the injection device relatively easily.

The outer surface of the compressible body may have a step profile at a location between the proximal end of the compressible body, which is configured to be inserted into the injection device, and an adjacent part of the compressible body, which is configured to remain outside of injection device, wherein the proximal end of the compressible body has a smaller diameter than the adjacent part of the compressible body.

This can allow the retention of the needle shield and cap component in the injection device prior to use whilst allowing the user to remove the cap and expose the needle for injection using the injection device relatively easily whilst allowing the overall injection device to be provided with an aesthetic appearance.

The outer diameter of the proximal end of the compressible body may be, when the compressible body is in an uncompressed state, greater than an internal diameter of the injection device into which the compressible body is insertable.

This ensures compression of the proximal end of the needle shield and cap component when it is located on the injection device, which can help to retain the cap and needle shield component in the injection device through friction prior to it being prepared for use by a user.

The outer diameter of the proximal portion of the component may be greater than 1 cm when in an uncompressed state.

The grip portion may comprise a surface that faces at least partially in a proximal direction relative to the longitudinal axis of the component.

The grip portion may comprise a head portion located distally from a neck portion. This can provide a particularly effective grip portion whilst being simple in configuration and high in manufacturability.

The cavity may additionally be tapered, which can help to reduce the chance of needle damage when the cap is removed from the injection device by a user.

The unitary compressible body may further comprise a needle holder cavity for tightly abutting a needle holder of an injection device, the needle holder cavity extending axially from its opening at the first end of the component and being shaped to coincide with the shape of the needle holder of the injection device. If such a needle holder cavity is included in the unitary compressible body, then the cavity for shielding a needle adjoins the needle holder cavity and extends axially within the component.

In another embodiment, an injection device is provided. The injection device includes a component as described above and the component acts to close an end of the injection device.

The injection device may include medicament.

The injection device may comprise a cartridge at least partly full of medicament.

Another embodiment is a method. The method comprises inserting a sheath containing a combined needle shield and cap component into a housing or a syringe carrier. The component comprises a unitary compressible body moulded from rubber. When uncompressed, the component has a larger outer diameter than the inner diameter of the sheath, such that the component is compressed whilst inside the sheath. The component also has formed therein a cavity for shielding a needle, the cavity having an opening at a first end of the component and extending axially within the component. The component also has formed thereon a grip arrangement comprising one or more shape features that permit gripping by a user of the component so as to facilitate the application of force by the user along the longitudinal axis of the component. The method also comprising removing the sheath, whilst leaving the component in the housing, so that the component expands and engages with one or more inner walls of the housing or syringe carrier.

The sheath may also contain a cartridge at least partly filled with medicament and having a needle assembly provided thereon, wherein a needle forming part of the needle assembly is provided within the cavity of the component.

The inner surface of the sheath may be a low friction surface.

Another aspect is a system comprising an injection device (10) and a combined needle shield and cap component (12) closing an end (123) of the injection device, wherein the combined needle shield and cap component comprises: a unitary compressible body moulded from rubber having formed therein a cavity for shielding a needle (17), the cavity having an opening at a first end of the combined needle shield and cap component and extending axially within the combined needle shield and cap component, and having has formed thereon a grip arrangement (122) comprising one or more shape features that permit gripping by a user of the combined needle shield and cap component so as to facilitate the application of force by the user in a distal direction along the longitudinal axis of the component, wherein a proximal end (125) of the unitary compressible body is located within a body of the injection device at the end of the injection device, wherein the outer surface of the unitary compressible body has a step profile at a location between the proximal end of the compressible body and an adjacent part (126) of the unitary compressible body, the location coinciding with an end of the body of the injection device with the adjacent part of the unitary compressible body being external to the body of the injection device, and wherein the proximal end of the unitary compressible body has a smaller diameter than the adjacent part of the unitary compressible body.

The outer diameter of the proximal portion of the component may be greater than 1 cm when in an uncompressed state.

The grip portion may comprise a surface that faces at least partially in a proximal direction relative to the longitudinal axis of the component.

The grip portion may comprise a head portion located distally from a neck portion.

The cavity may be tapered.

The unitary compressible body may further comprise a needle holder cavity for tightly abutting a needle holder of an injection device, the needle holder cavity extending axially from its opening at the first end of the component and being shaped to coincide with the shape of the needle holder of the injection device; and the cavity for shielding a needle adjoins the needle holder cavity and may extend axially within the component.

The injection device may include medicament.

The injection device may comprise a cartridge at least partly full of medicament.

"The terms "drug" or "medicament" which are used interchangeably herein, mean a pharmaceutical formulation that includes at least one pharmaceutically active compound.

BRIEF DESCRIPTION OF THE DRAWINGS

Exemplary embodiments of the present invention are described with reference to the accompanying drawings, in which.

DETAILED DESCRIPTION

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1A:
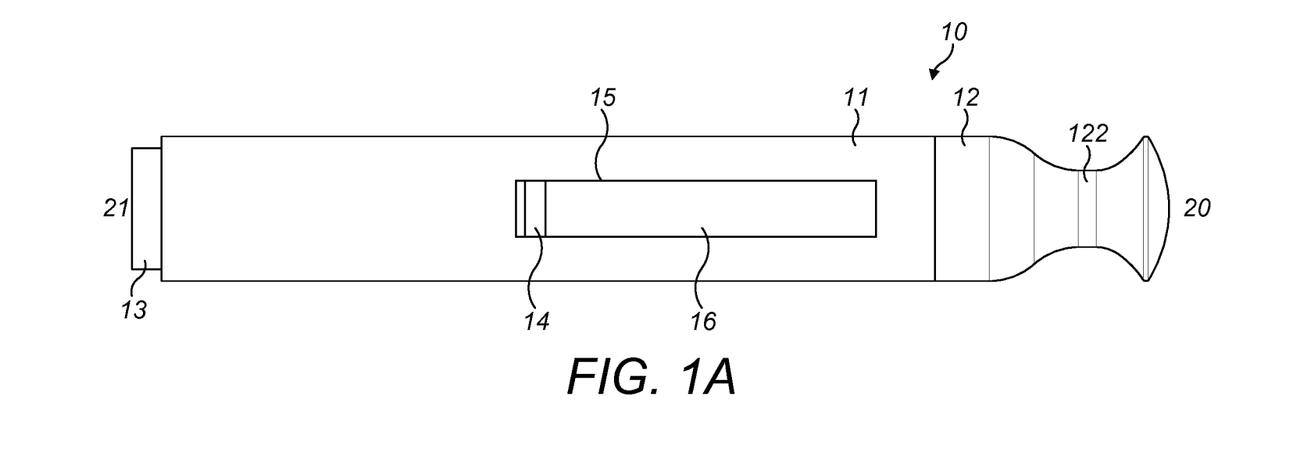
FIGS. 1A and 1B—together referred to as FIG. 1—are isometric views of an injection device according to one or more embodiments.
Figure 1B:
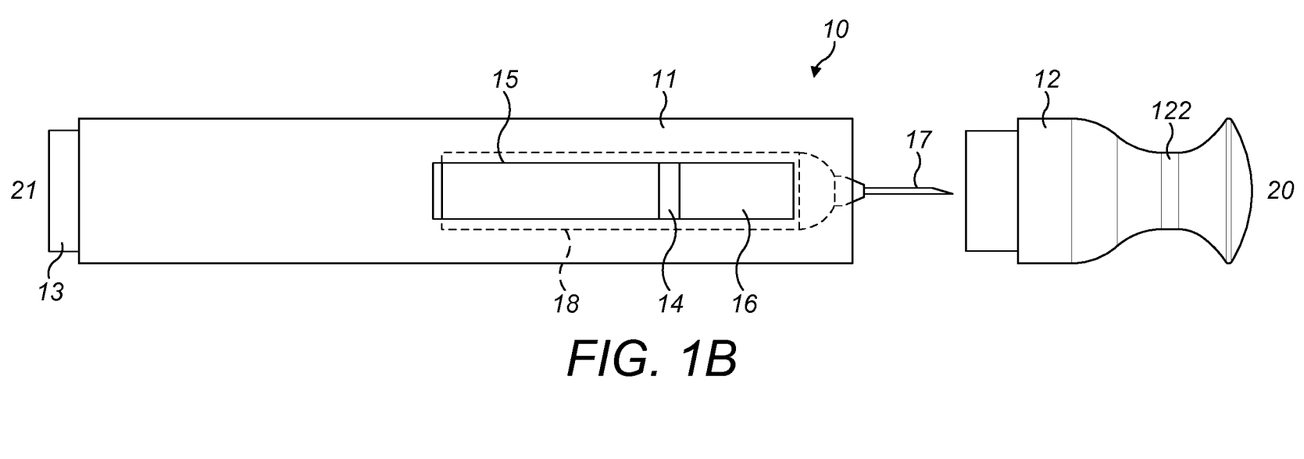

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. Device 10 can also include a cap assembly 12 that can be detachably mounted to the housing 11. Typically a user removes cap 12 from housing 11 before device 10 can be operated.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Insertion of needle 17 can occur via several mechanisms, for example manually or automatically. In "automated" insertion, insertion can be triggered by movement of, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 21 of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe, forcing it out of needle 17.

Following injection, needle 17 can be retracted within housing 11.

Needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 13 or other components of device 10 can be locked as required.

Figure 2:
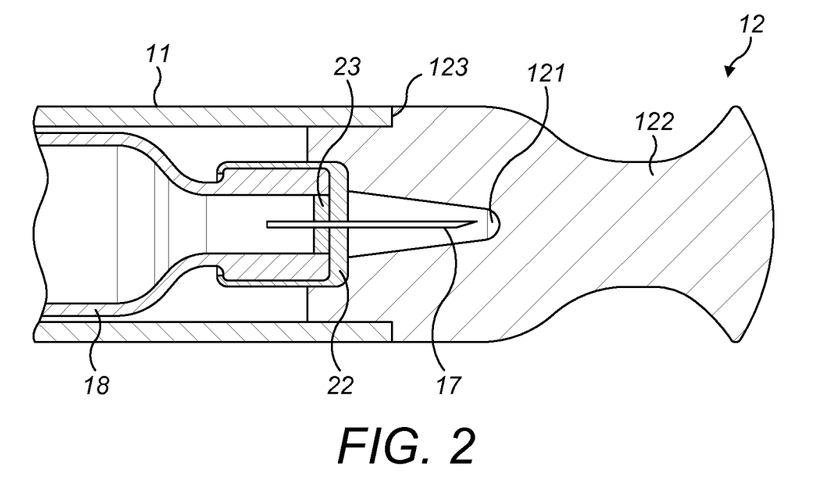
FIG. 2 is a cross-sectional view of the injection device of FIG. 1.

FIG. 2 is an enlarged, cross-sectional view of the auto-injector device 10 shown in FIGS. 1A and 1B. The cartridge 18 is disposed within the housing 11 of the auto-injector device 10. One end of the needle 17 is disposed within the cartridge 18, such that the needle 17 is in fluid connection with the volume defined by the cartridge 18. The other end of the needle 17 extends axially from the cartridge 18 and protrudes out from the mouth of the housing 11. The needle 17 lies on the longitudinal axis of the auto-injector device 10.

The needle 17 is attached to the cartridge 18 by way of a needle holder 22. The needle 17 extends through an aperture in the centre of a septum 23 provided at the mouth of the cartridge 18 and forms a seal therewith. The outer surface of the septum 23 tightly abuts the inner surface of the cartridge 18, thus forming a seal therewith preventing liquid from escaping from the cartridge. The needle holder 22 is made of a rigid material and holds the needle 17 in place. The needle holder 22 is crimped over the head of the cartridge 18 to secure it in place, as can be seen in FIG. 2.

In an initial state (depicted in FIG. 2) of the auto-injector device 10, the cap 12 is attached at the distal end of the auto-injector device 10 to seal the distal end of the housing 11 and shield the needle 17. Some of the features of the cap 12 can be seen more easily from FIG. 3.

Figure 3:
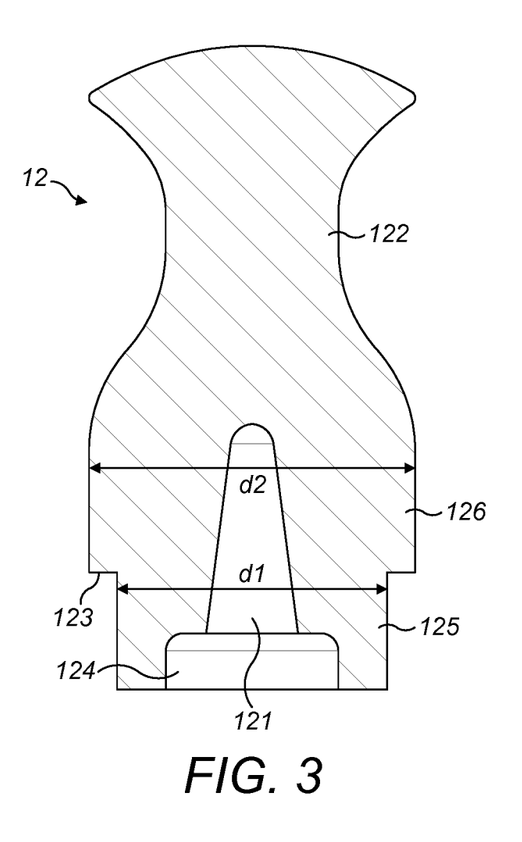
FIG. 3 is a cross-sectional view of a cap forming part of the injection device of FIG. 1.

The cap 12 is a unitary body. The cap 12 may be moulded from rubber. For instance the cap 12 may be moulded using an injection moulding process. The cap 12 may be moulded from synthetic rubber or natural rubber, or a mixture thereof. The cap 12 may be compressed by about 10-20% under elastic deformation; i.e. the cap 12 can be compressed by 10-20% by volume under an external force of between 20 and 50 Newtons, then return to its original size and shape after the force is removed.

The cap 12 defines a needle holder cavity 124 which is centred about the longitudinal axis of the cap 12 and has an opening at the proximal end of the cap 12. The shape of the needle holder cavity 124 coincides with that of at least a portion of the outer surface of the needle holder 22. The shape of the needle holder cavity 124 may correspond closely to the shape of the outer surface of the needle holder 22. Alternatively, the needle holder cavity 124 may be slightly smaller in the radial direction. In this way, when the needle holder 22 is disposed within the cap 12 (as in FIG. 2), the cap 12 tightly abuts the needle holder 22, securing the two together by way of frictional forces and forming a seal between the cap 12 and the needle holder 22. If the needle holder cavity 124 is slightly smaller in diameter than the diameter of the outer surface of the needle holder 22 when the cap 12 is in an uncompressed state, then the cap 12 applies a radially inward force to the outer surface of the needle holder 22, thereby increasing the frictional force between the cap 12 and the needle holder 22.

The cap 12 defines a needle shield cavity 121, which extends from the needle holder cavity 124, for shielding the needle 17. The needle shield cavity 121 has an opening at the proximate end of the needle holder cavity 124 and extends part-way through the cap 12 along its longitudinal axis. The length of the needle shield cavity 121 is greater than the length of the part of the needle 17 that extends distally from the needle holder 22. As such, the needle 17 and the cap 12 do not contact one another. The needle shield cavity 121 is generally frusto-conical in shape. Such a shape reduces the possibility of the cap 12 and needle 17 coming into contact if the cap is pulled off at an angle.

The seal between the needle holder cavity 124 and the needle holder 22 isolates the needle 17 from the external environment, thereby ensuring that the needle 17 remains sterile before the cap 12 is removed.

The outer surface of the cap 12 defines a step 123 where the outer diameter of the cap 12 changes discontinuously. A first portion 125 of the cap 12, located at its proximal end, has a diameter, d1. The length of the first portion 125 is equal to the longitudinal separation between the proximal face of the needle holder 22 and the proximal end of the housing 11, plus the length of the needle holder cavity 124. A second portion 126 of the cap 12, located immediately adjacent to the first portion 125, has a diameter d2, wherein d1<d2. The step 123 is located at the boundary of the first and second portions 125, 126. In the initial state of the auto-injector device 10, the first portion 125 of the cap 12 is disposed within the housing 11, whilst the second portion 126 is external to the housing. Accordingly, the step 123 abuts the distal end of the housing 11.

When the cap 12 is in an uncompressed state, the first diameter d1 is equal to, or slightly larger than, the inner diameter of the housing 11. Therefore, when located within the housing 11, the outer surface of the first portion 125 tightly abuts the inner surface of the housing 11. This tightly abutting relationship secures the cap 12 within the housing 11 by way of frictional forces. If d1 is slightly larger than the inner diameter of the housing 11 when in an uncompressed state, then the first portion 125 of the cap 12 applies a radially outward force to the inner wall of the housing 11, thereby increasing the frictional force between the cap 12 and the housing 11.

The diameter d2 is equal to the diameter of the outer surface of the housing 11 so that, in the initial state shown in FIG. 2, the outer surfaces of the housing 11 and the second portion 126 coincide in the radial plane. This provides a smooth join between the cap 12 and the housing 11. This helps to provide an aesthetic appearance for the auto-injector device 10.

The cap 12 has a grip portion 122 at its distal end. The grip portion 122 in this embodiment consists of a neck portion located immediately adjacent to a head portion, wherein the head portion is located at the very end of the cap 12 (distal end). The neck has a smaller diameter than the head. In particular, the diameter of the head portion is the same as that of the second portion 126 (d2). The diameter of the neck portion is approximately half the diameter of the head portion. The head portion is rounded at its distal end. The grip portion allows the user to grip the cap 12 more effectively in order to apply force along its longitudinal axis. This makes it easier for a user to remove the cap 12 by hand.

Figure 4A:
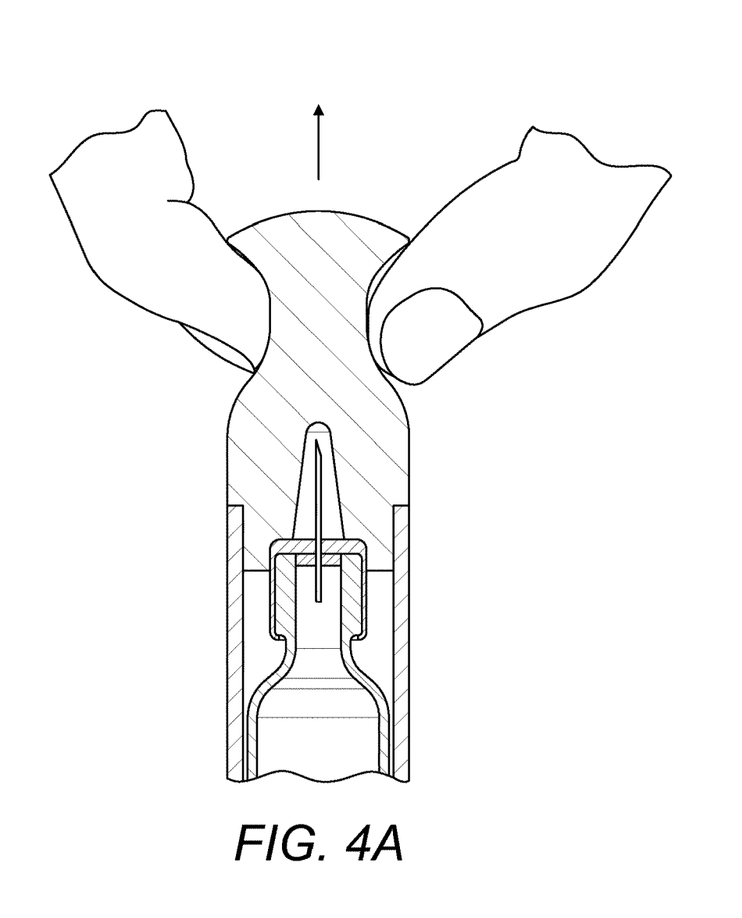
FIGS. 4A and 4B are cross-sectional views of the injection device of FIG. 1 as the cap is removed by a user.
Figure 4B:
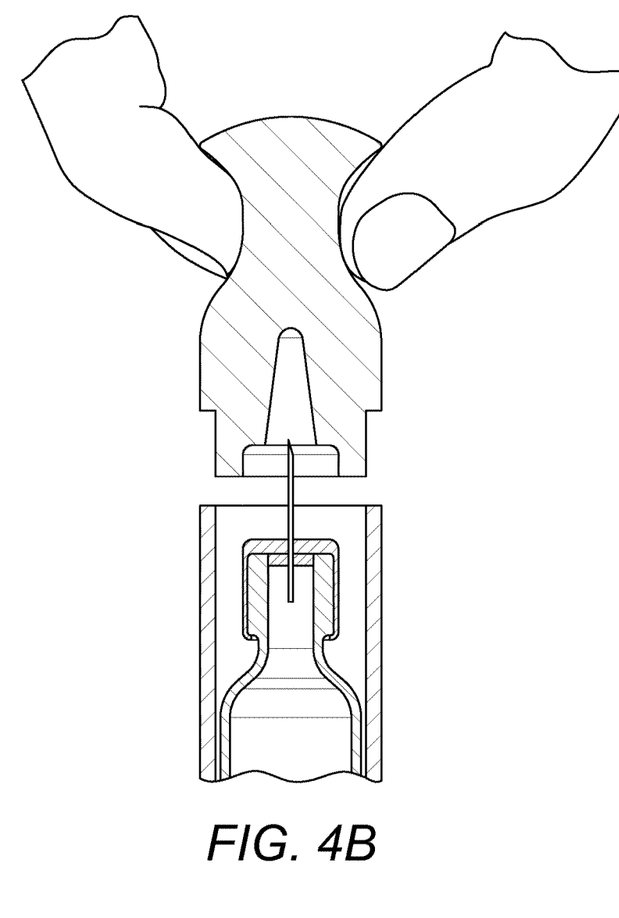

FIGS. 4A and 4B show a user pulling off the cap 12 by hand. FIG. 4A shows the user gripping the cap 12 whilst the cap is in place on the auto-injector device 10.

FIG. 4B shows the cap 12 removed in the distal direction after the user applied a force in the distal direction.

An advantage of the auto-injector device 10 is that it is simple to use. In particular, to ready the auto-injector device 10 for use, a user can simply pull the cap 12 off by hand. There is no removal of a cap then removal of an inner needle shield, as is required with some prior art devices.

The cap 12 removes the need for a cap and a separate needle shield arrangement. This may reduce the costs of manufacture compared to a corresponding arrangement with multiple components.

Since the diameter of the cap 12 is the same as the diameter of the auto-injector device 10, the cap 12 is of a relatively large size. This makes the cap 12 more suitable for manipulation by a human hand than, for example, a conventional inner needle shield.

The tightly fitting relationship between the cap 12 and the inner surface of the housing 11 means that only a force applied in the longitudinal direction will remove the cap 12 from the housing 11. This encourages the user to apply force predominantly along the longitudinal axis, when pulling off the cap. An advantage of this is that the user is less likely to angle or tilt the cap 12 away from the longitudinal direction when removing the cap. Since angling or tilting the cap 12 could result in the cap 12 coming into contact with and damaging the needle 17, the arrangement of the cap 12 may reduce the possibility of damage of the needle 17 when the user removes the component (the cap 12) that shields the needle 17 before use.

A further advantage is that, whilst in the initial state (FIG. 2), the cap 12 simultaneously closes the distal end of the housing 11, shields the needle 17 such as to avoid the possibility of needle stick injury, and isolates the needle from the external environment to maintain sterility of the needle 17.

Figure 7A:
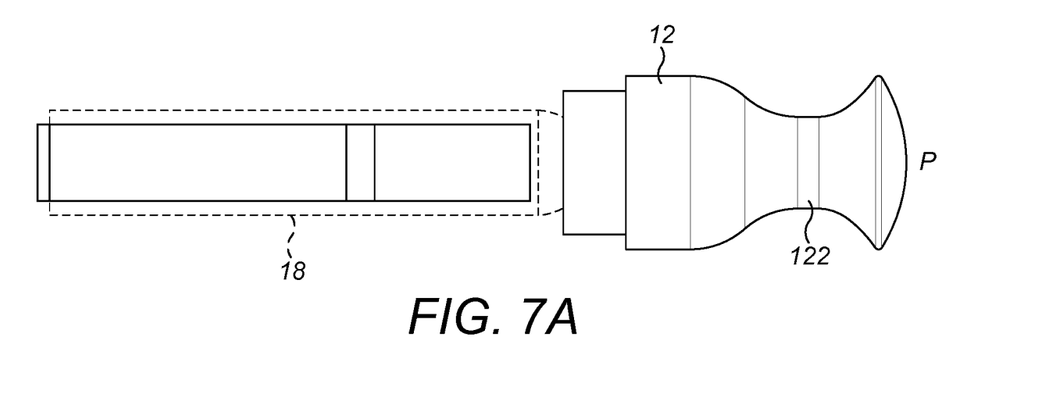
FIGS. 7A-7E show several stages of the assembly of the injection device of FIG. 1.
Figure 7B:
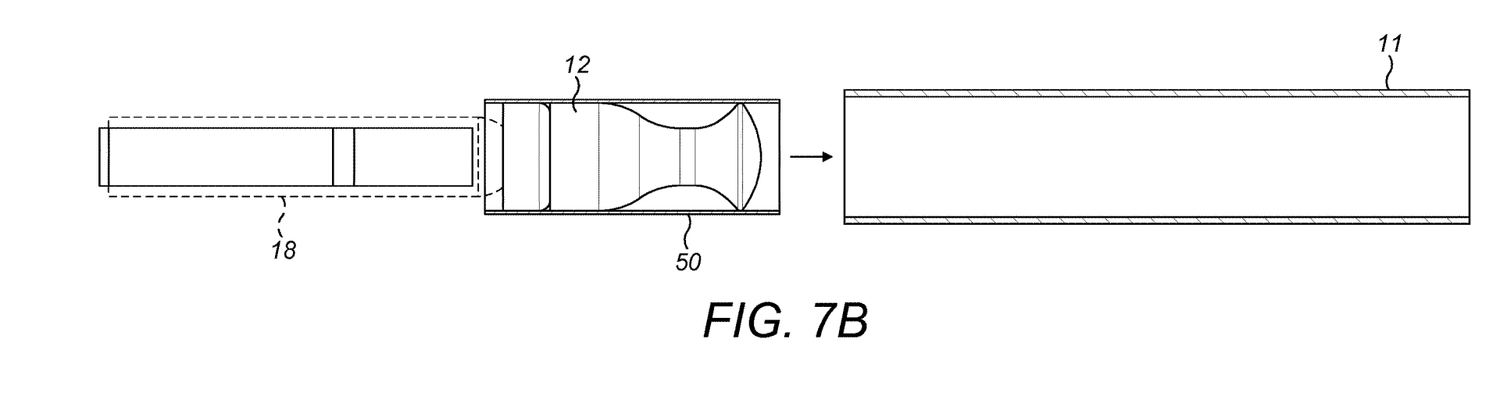

FIGS. 5, 6 and 7A-7E illustrate a method of inserting the cap 12 into the housing 11 of the auto-injector device 10. The cap 12 is positioned on the cartridge 18 as in FIG. 2. Here, the needle holder 22 is installed on the head of the cartridge 18 and is located within the needle holder cavity 124. The needle 17 is located within the needle shield cavity 121. The cartridge 18 and the cap 12 are external to the housing 11 at this point, as shown in FIGS. 7A and 7B.

The cap 12, cartridge 18 and needle 17 are housed within a hollow cylinder 50, which constitutes a sheath (see FIG. 7B). The hollow cylinder 50 is made of an inflexible material, such as steel. The outer diameter of the hollow cylinder 50 is smaller than the diameter of the inner surface of the housing 11. Therefore the cap 12 is compressed whilst within the hollow cylinder 50. The inner surface of the hollow cylinder can be a low friction surface, either by being provided with a low friction coating (such as PTFE) or by being provided with a lubricant liquid or gel. The lubricant is sterile, and may be disinfectant.

Figure 7C:
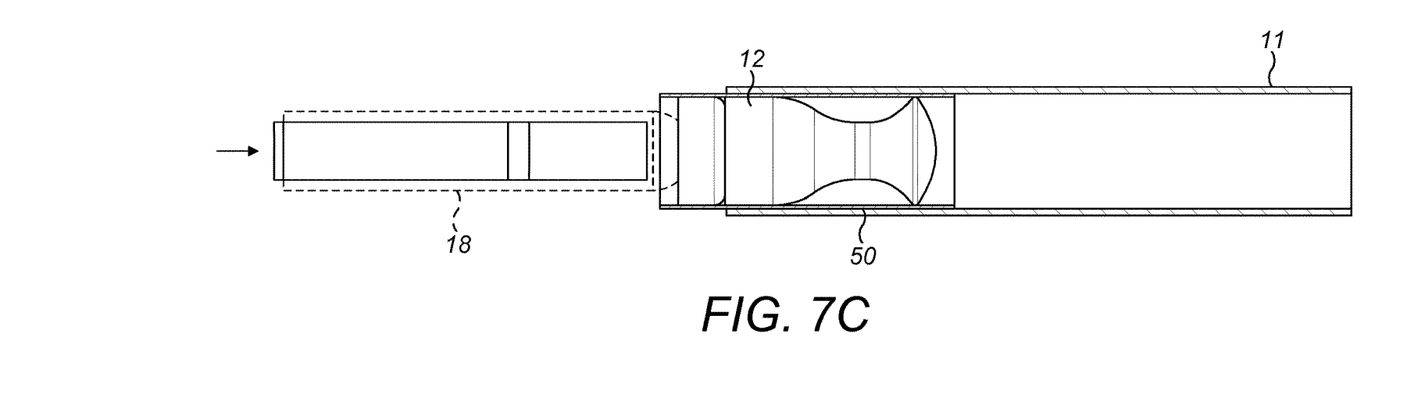
Figure 7D:
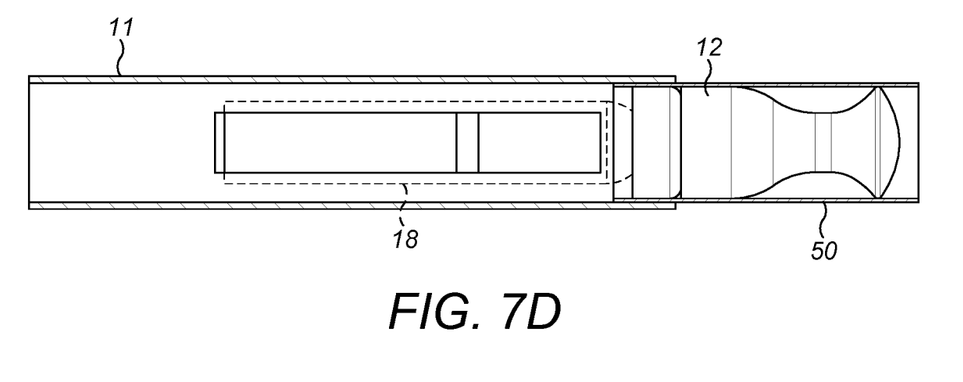
Figure 7E:
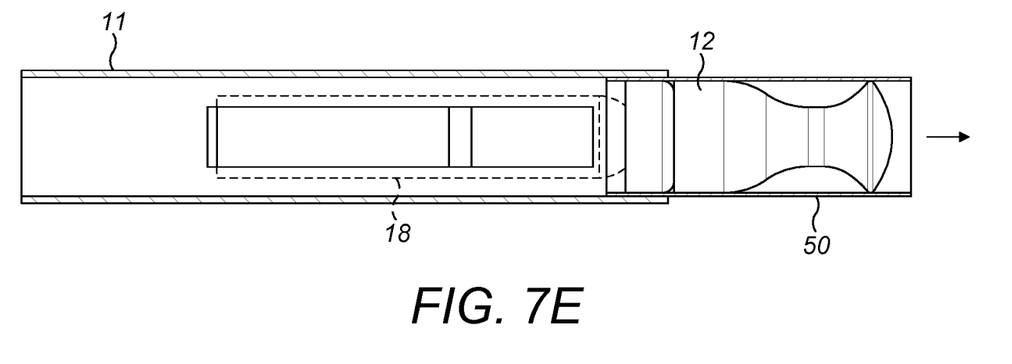

The hollow cylinder 50, with the cap 12, cartridge 18 and needle 17 contained within it, is then inserted into the housing 11 (step S2) at its proximal end, as can be seen in FIGS. 7B and 7C. Next the position of the hollow cylinder 50 within the housing 11 is adjusted until the cap 12 and cartridge 18 are properly aligned with the housing 11 (step S3); i.e. so that the step 123 is inline with the distal edge of the housing 11. This is done by moving the hollow cylinder 50, cartridge 18 and cap 12 along the housing 11 to its distal end, as shown in FIG. 7D. At this stage, a cartridge holder (not shown) may be caused to engage with the cartridge 18 so as to retain the cartridge 18 in place.

Figure 5:
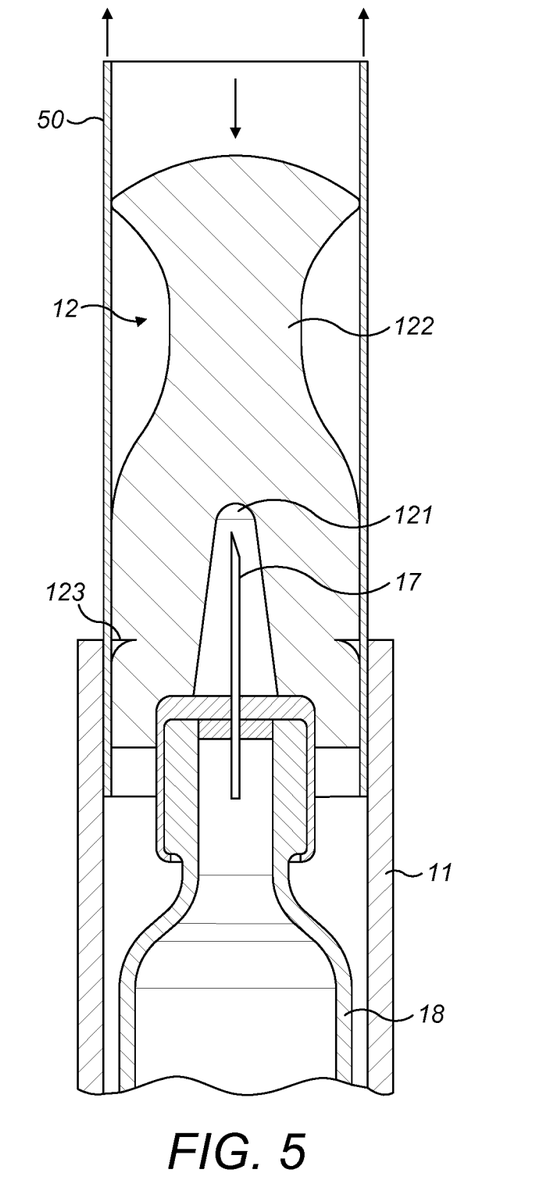
FIG. 5 is a cross-sectional view of the injection device of FIG. 1 at one stage of its assembly.
Figure 6:
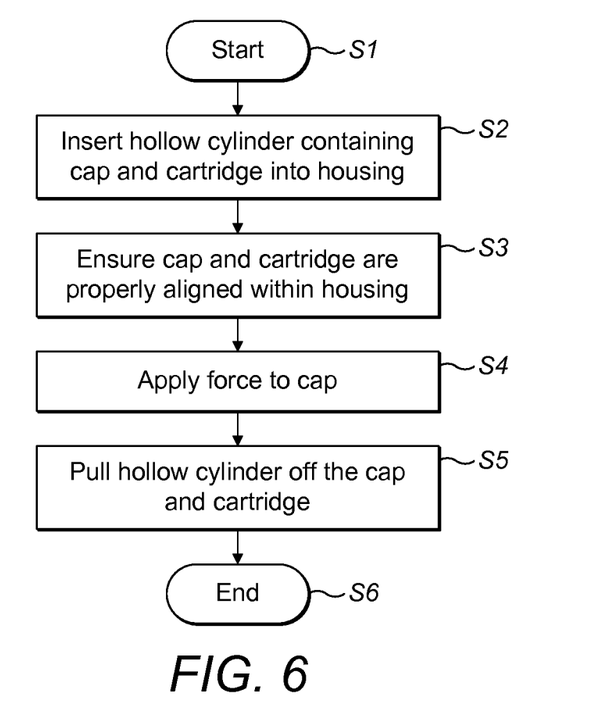
FIG. 6 is a flow chart showing a method of assembling the injection device of FIG. 1.

Once in place, a force is applied to the distal end of the cap 12 in the longitudinal direction (step S4), whilst the hollow cylinder 50 is moved in the distal direction (upwards as shown in FIG. 5). This causes the cylinder 50 to be pulled off the cap 12 and cartridge 18 (step S5) (also shown in FIG. 7E). The force applied to the cap 12 is sufficient to keep the cap 12 and cartridge 18 stationary within the housing 11 as the hollow cylinder 50 is removed. The low friction surface or lubricant assists in minimising or preventing movement of the cap 12 as the cylinder 50 is removed. The hollow cylinder 50 may be initially located such that the step 123 is located a small distance along the axis in the distal direction. The distance is chosen such that the step 123 locates at the distal edge of the housing 11 when the cylinder is removed due to compression of the cap 12 in the axial direction as the cylinder 50 is removed from the cap 12.

Once the hollow cylinder 50 is removed, the cap 12 expands towards its uncompressed size and the first portion 125 abuts the inner surface of the housing 11, securing the cap 11 in place. With the hollow cylinder 50 removed, the auto-injector device 10 is in the state shown in FIG. 2.

The above embodiments are not intended to be limiting and many other embodiments and alternatives are within the scope of the appended claims. Some such embodiments and alternatives will now be described.

The exact form of the cartridge 18 is not important, and any suitable cartridge may be used in place of the cartridge 18.

Although the embodiments are described in relation to an auto-injector device, other embodiments are different single-use devices, such as single-use syringes.

In some embodiments, the needle holder cavity 124 described above may not be provided. For instance, in some embodiments, the proximal end of the cap 12 is configured to abut the needle holder 22, when the cap 12 is fully inserted into the housing 11. In some embodiments, the cap does not include a needle holder cavity 124 and the needle shield cavity 121 is the same as in the embodiment described above, except that it extends from the proximal end of the cap 12. In some embodiments, the needle shield cavity 121 may be the only cavity in the cap 12.

In some embodiments, the needle shield cavity 121 may be reinforced with a strong, rigid material (e.g. a suitable plastic). This prevents the needle shield cavity 121 from deforming as a result of the compression of the cap 12 or as the result of shear stress; e.g. if the user pulls the cap 12 off at an angle from the longitudinal direction. Some embodiments have the advantage that the cap 12 is further less likely to come into contact with the needle 17, thus providing further immunity to damaging of the needle 17 as the shield (cap 12) is removed.

Although described above as being frusto-conical in shape, the needle shield cavity 121 may take any appropriate shape. For example the needle shield cavity 121 could be cylindrical, semi-ellipsoidal, a square-prism, a triangular prism etc.

In an alternative assembly of the auto-injector device 10, the hollow cylinder 50, with the cap 12, cartridge 18 and needle 17 contained within it, may be inserted into the housing 11 from its distal end, rather than its proximal end.

Instead of being mountable directly within the housing 11, the cap 12 may be insertable and retainable in a needle sleeve (not shown) that is mounted directly within the housing 11. Here, the device 10 can also include the needle sleeve coupled to housing 11 to permit movement of the sleeve relative to housing 11. For example, the sleeve can move in a longitudinal direction parallel to the longitudinal axis. Specifically, movement of the sleeve in a proximal direction can permit needle 17 to extend from the distal end of housing 11. For example, needle 17 may be fixedly located relative to housing 11 and initially be located within an extended needle sleeve. Proximal movement of the sleeve by placing a distal end of the sleeve against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to the sleeve.

Another form of insertion is "automated," whereby needle 17 moves relative to housing 11. Such insertion can be triggered by movement of the sleeve or by another form of activation, such as, for example, button 13. As shown in FIGS. 1A & 1B, button 13 is located at a proximal end of housing 11. However, in other embodiments, button 13 could be located on a side of housing 11.

Following injection, needle 17 can be retracted within the sleeve or housing 11. Retraction can occur when the sleeve moves distally as a user removes the device 10 from a patient's body. This can occur as needle 17 remains fixedly located relative to housing 11. Once a distal end of the sleeve has moved past a distal end of needle 17, and needle 17 is covered, the sleeve can be locked. Such locking can include locking any proximal movement of the sleeve relative to housing 11.

In some embodiments, although the method shown in FIGS. 5, 6 and 7A-7E is for inserting the cap 12 into the housing 11 of the auto-injector device 10, the cap 12 may be inserted into a syringe carrier (rather than the housing 11) in the same way.

In some embodiments, the grip portion 122 may take on other forms from the neck and head described above and shown in the figures. For instance, the grip portion 122 may take the form of circumferential ridges on the outer surface of the cap 12. Alternatively a ring may be provided at the distal end of the cap 12 for a user to put their finger through in order to more easily apply a force to the cap in the longitudinal direction. In general terms, the grip portion 122 provides a surface that forms a non-zero angle (θ) with the longitudinal axis. Advantageously, the angle θ is at least 45 degrees. In other embodiments, θ is at least 20 degrees or more advantageously at least 30 degrees. The surface of the grip portion may be curved, as it is in the embodiments shown in the Figures. In the case of a curved grip surface, at least a part of the surface has a tangent which forms an angle θ with the longitudinal axis as described above.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-human insulin; B29-N-(ω-carboxyheptadecanoyl)-des(B30) human insulin and B29-N-(ω-carboxyhepta-¬decanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

The invention claimed is:

1. A component for an injection device comprising:
 a unitary compressible body moulded from rubber, wherein the unitary compressible body:
  has formed therein a cavity for shielding a needle, the cavity having an opening at a first end of the component and extending axially within the component;
  has formed thereon a grip arrangement comprising one or more shape features that permit gripping by a user of the component so as to facilitate the application of force by the user along a longitudinal axis of the component; and
  has a proximal end configured to be partly insertable into a body of an injection device,
 wherein an outer surface of the compressible body has a step profile at a location between the proximal end of the compressible body and an adjacent part of the compressible body, wherein a distal end of the compressible body is configured to be inserted into the injection device and the adjacent part of the compressible body is configured to remain outside of the injection device, wherein the proximal end of the compressible body has a smaller diameter than the adjacent part of the compressible body,
 wherein an outer diameter of the proximal end of the compressible body is greater than an internal diameter of the injection device into which the compressible body is insertable when the compressible body is in an uncompressed state.

2. A component as claimed in claim 1, wherein an outer diameter of a proximal portion of the component is greater than 1 cm when the component is in an uncompressed state.

3. A component as claimed in claim 1, wherein the grip arrangement comprises a surface that faces at least partially in a proximal direction relative to the longitudinal axis of the component.

4. A component as claimed in claim 1, wherein the grip arrangement comprises a head portion located distally from a neck portion.

5. A component as claimed in claim 1, wherein the cavity is tapered.

6. A component as claimed in claim 1, wherein the unitary compressible body comprises a needle holder cavity for tightly abutting a needle holder of the injection device, the needle holder cavity extending axially from the opening at the first end of the component and being shaped to coincide with a shape of the needle holder of the injection device; and
 wherein the cavity for shielding the needle adjoins the needle holder cavity and extends axially within the component.

7. An injection device including the component according to claim 1, the component configured to close an end of the injection device.

8. An injection device according to claim 7, including medicament.

9. An injection device according to claim 8 comprising a cartridge at least partly full of medicament.

10. A system comprising an injection device and a combined needle shield and cap component closing an end of the injection device, wherein the combined needle shield and cap component comprises:
a unitary compressible body moulded from rubber having formed therein a cavity for shielding a needle, the cavity having an opening at a first end of the combined needle shield and cap component and extending axially within the combined needle shield and cap component, the compressible body having formed thereon a grip arrangement comprising one or more shape features that permit gripping by a user of the combined needle shield and cap component so as to facilitate the application of force by the user in a distal direction along a longitudinal axis of the combined needle shield and cap component,
wherein a proximal end of the compressible body is located within a body of the injection device at the end of the injection device,
wherein an outer surface of the compressible body has a step profile at a location between the proximal end of the compressible body and an adjacent part of the compressible body, the location coinciding with an end of the body of the injection device with the adjacent part of the compressible body being external to the body of the injection device, and
wherein the proximal end of the compressible body has a smaller diameter than the adjacent part of the compressible body,
wherein an outer diameter of the proximal end of the compressible body is greater than an internal diameter of the injection device into which the compressible body is insertable when the compressible body is in an uncompressed state.

11. A system as claimed in claim 10, wherein an outer diameter of a proximal portion of the combined needle shield and cap component is greater than 1 cm when the combined needle shield and cap component is in an uncompressed state.

12. A system as claimed in claim 10, wherein the grip arrangement comprises a surface that faces at least partially in a proximal direction relative to the longitudinal axis of the combined needle shield and cap component.

13. A system as claimed in claim 10, wherein the grip arrangement comprises a head portion located distally from a neck portion.

14. A system as claimed in claim 10, wherein the cavity is tapered.

15. A system as claimed in claim 10, wherein the unitary compressible body comprises a needle holder cavity for tightly abutting a needle holder of the injection device, the needle holder cavity extending axially from the opening at the first end of the combined needle shield and cap component and being shaped to coincide with a shape of the needle holder of the injection device; and
wherein the cavity for shielding the needle adjoins the needle holder cavity and extends axially within the combined needle shield and cap component.

16. A system according to claim 10, wherein the injection device includes medicament.

17. A system according to claim 10, wherein the injection device comprises a cartridge at least partly full of medicament.

18. A method comprising:
inserting a sheath containing a combined needle shield and cap component into a housing or a syringe carrier of an injection device, wherein the combined needle shield and cap component:
comprises a unitary compressible body moulded from rubber;
has a larger outer diameter than an inner diameter of the sheath when the combined needle shield and cap component is uncompressed, such that the combined needle shield and cap component is compressed whilst inside the sheath;
has formed therein a cavity for shielding a needle, the cavity having an opening at a first end of the combined needle shield and cap component and extending axially within the combined needle shield and cap component;
has formed thereon a grip arrangement comprising one or more shape features that permit gripping by a user of the combined needle shield and cap component so as to facilitate the application of force by the user along a longitudinal axis of the combined needle shield and cap component;
has a proximal end configured to be partly insertable into a body of the injection device; and
includes a step profile on an outer surface of the compressible body at a location between the proximal end of the compressible body and an adjacent part of the compressible body, wherein the proximal end of the compressible body is configured to be inserted into the injection device and the adjacent part of the compressible body is configured to remain outside of the injection device, wherein the proximal end of the compressible body has a smaller diameter than the adjacent part of the compressible body; and
removing the sheath whilst leaving the combined needle shield and cap component in the housing so that the combined needle shield and cap component expands and engages with one or more inner walls of the housing or syringe carrier.

19. A method as claimed in claim 18 wherein the injection device contains a cartridge at least partly filled with medicament and having a needle assembly provided thereon, wherein the needle forming part of the needle assembly is provided within the cavity of the combined needle shield and cap component.

20. A method as claimed in claim 18 wherein an inner surface of the sheath is a low friction surface.

* * * * *